US011085909B1

(12) United States Patent
Berg et al.

(10) Patent No.: US 11,085,909 B1
(45) Date of Patent: Aug. 10, 2021

(54) METHODS AND SYSTEMS FOR CHARACTERIZING CLAY

(71) Applicant: ADVANCED AGRILYTICS HOLDINGS, LLC, Huntington, IN (US)

(72) Inventors: William Kess Berg, Clayton, IN (US); Jon J. Fridgen, Tolono, IL (US)

(73) Assignee: ADVANCED AGRILYTICS HOLDINGS, LLC, Indianapolis, IN (US)

( * ) Notice: Subject to any disclaimer, the term of this patent is extended or adjusted under 35 U.S.C. 154(b) by 0 days.

(21) Appl. No.: 16/948,613

(22) Filed: Sep. 24, 2020

(51) Int. Cl.
*G01N 33/00* (2006.01)
*G01N 33/24* (2006.01)
*G01N 35/00* (2006.01)
*A01B 79/00* (2006.01)
*G16C 60/00* (2019.01)
*A01C 21/00* (2006.01)

(52) U.S. Cl.
CPC ............ *G01N 33/24* (2013.01); *A01B 79/005* (2013.01); *G01N 35/00722* (2013.01); *G16C 60/00* (2019.02); *A01C 21/005* (2013.01); *A01C 21/007* (2013.01); *G01N 2033/245* (2013.01); *G01N 2035/0091* (2013.01); *G01N 2035/00841* (2013.01)

(58) Field of Classification Search
CPC ....... A01B 79/02; A01B 79/00; A01B 79/005; A99Z 99/00; G01N 33/24; G01N 35/00722; G01N 2035/0091; G01N 2035/00841; G01N 2033/245; G16C 60/00; A01C 21/005; A01C 21/007
See application file for complete search history.

(56) References Cited

U.S. PATENT DOCUMENTS

| | | | | |
|---|---|---|---|---|
| 2016/0360755 | A1* | 12/2016 | Al Juhaiman | ......... A01N 25/04 |
| 2019/0106637 | A1* | 4/2019 | Oswald | ................... C05D 9/00 |
| 2019/0124853 | A1* | 5/2019 | Serizawa | ............. A01B 79/005 |
| 2019/0289786 | A1* | 9/2019 | Prystupa | ................. A01F 12/44 |
| 2019/0313589 | A1* | 10/2019 | Johnson | ................. G08B 21/18 |

* cited by examiner

*Primary Examiner* — Shogo Sasaki
(74) *Attorney, Agent, or Firm* — Marshall, Gerstein & Borun LLP

(57) ABSTRACT

A method of improving agricultural treatment includes collecting a machine data set, analyzing the machine data set to identify a mineralogical feature, generating a clay characterization by analyzing the mineralogical feature, and generating an agricultural prescription. A system includes a processor and a memory storing instructions that, when executed by the processor, cause the system to collect a machine data set, analyze the machine data set to identify a mineralogical feature, generate a clay characterization by analyzing the mineralogical feature, and generate an agricultural prescription. A non-transitory computer readable medium containing program instructions that when executed, cause a computer to collect a machine data set, analyze the machine data set to identify a mineralogical feature, generate a clay characterization by analyzing the mineralogical feature, and generate an agricultural prescription.

20 Claims, 6 Drawing Sheets

US 11,085,909 B1

METHODS AND SYSTEMS FOR CHARACTERIZING CLAY

TECHNICAL FIELD

The present disclosure is generally directed to methods and systems for characterizing clay, and more specifically, for generating field management recommendations based on one or more determined clay types within a field and/or sub-field.

BACKGROUND

Growers and trusted advisors struggle to gain a comprehensive understanding of the behavior of clay soils in agricultural fields. For example, understanding mineral fraction in terms of percentage of sand, silt and clay is essential for growers seeking to treat their fields. It is further essential that growers are able to measure and understand soil organic matter content.

Yet conventional agricultural growing techniques do not take into account the different varieties of clay, including differing lattice structures found in clay based on differing clay content ratios (e.g., a 2:1 clay, a 1:1 clay, etc.). For example, a grower/trusted advisor may not be able to determine soil clay characteristics relating to one or more fields of the grower. The grower/trusted advisor may sample a portion of one or more fields and discover a clay content type (e.g., vermiculite) and not realize that other areas of the one or more fields include additional clay content types. The grower may not be able to measure organic matter directly or indirectly.

BRIEF SUMMARY

In one aspect, a computer-implemented method of improving agricultural inputs/treatment application in clay soils within an agricultural field includes collecting a machine data set corresponding to the agricultural field, analyzing the machine data set to identify one or more mineralogical features, generating a set of clay characterizations by analyzing the mineralogical features, each of the characterizations corresponding to a respective hexagrid cell, and generating an agricultural prescription for the agricultural field, including at least one treatment based on the clay characterization.

In another aspect, a computing system includes one or more processors; and one or more memories storing instructions. When executed by the one or more processors, the instructions cause the computing system to collect a machine data set corresponding to the agricultural field, analyze the machine data set to identify one or more mineralogical features, generate a set of clay characterizations by analyzing the mineralogical features, each of the characterizations corresponding to a respective hexagrid cell, and generate an agricultural prescription for the agricultural field, including at least one treatment based on the clay characterization.

In yet another aspect, a non-transitory computer readable medium containing program instructions that when executed, cause a computer to collect a machine data set corresponding to the agricultural field, analyze the machine data set to identify one or more mineralogical features, generate a set of clay characterizations by analyzing the mineralogical features, each of the characterizations corresponding to a respective hexagrid cell, and generate an agricultural prescription for the agricultural field, including at least one treatment based on the clay characterization.

BRIEF DESCRIPTION OF THE FIGURES

The figures described below depict various aspects of the system and methods disclosed therein. It should be understood that each figure depicts one embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

Figure 1:
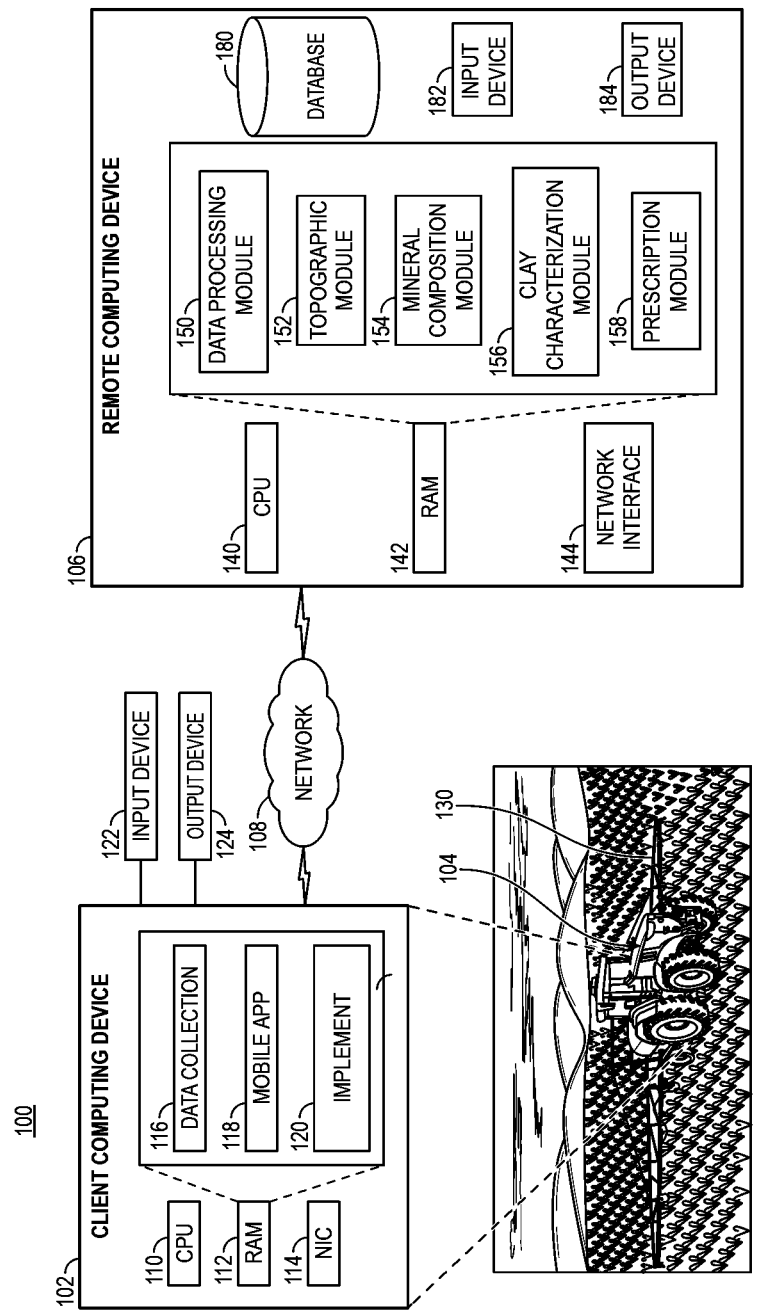
FIG. 1 depicts an exemplary computing environment, according to an embodiment.

The figures depict preferred embodiments for purposes of illustration only. One of ordinary skill in the art will readily recognize from the following discussion that alternative embodiments of the systems and methods illustrated herein may be employed without departing from the principles of the invention described herein.

DETAILED DESCRIPTION

Overview

The present disclosure is generally directed to methods and systems for characterizing clay, and more specifically, for generating field management recommendations based on one or more determined clay types within a field and/or sub-field.

The present techniques enable growers and trusted advisors to get a better picture of the clay soils in the agricultural fields that they own and/or manage. A mineral fraction within soil may include sand, silt and/or clay. The organic fractions are referred to as organic matter. Multiple types of clay are common, including 2:1, 1:1, etc. The ratios reflect the crystalline structure of clay lattices stacked together. The types of clay in a single field may vary greatly from sample to sample. Absorption and shrink-swell capacity are largely affected by clay type.

Clay is a product of geologic activity (e.g., glaciation) and more recent activity. For example, Lake Erie formerly extended to Fort Wayne, Ind. and into parts of the State of Ohio. Some of the areas in question were under water for millennia, and as such did not weather as much as surrounding areas, and thus have generally lower organic matter content. It is the case that clay samples taken from fields in Ohio formerly part of Lake Erie are more similar to clay samples taken from near the Mississippi River delta than they are to clay soils found in other parts of Ohio. In other places throughout the Midwest and other breadbasket farming areas, a 10-foot change in elevation may be evidence of an ancient beachhead, and a delimiter of two drastically different clay types. Consequently, growers can make severe mistakes by assuming that clay composition of soil is the same throughout a given field or farm. And as will be shown below, clay composition is highly predictive of agricultural yields, and thus, cannot be ignored by those engaging in the science of precision agriculture.

The present techniques assist growers and field managers in determining clay soil types and provide advantageous visualization tools to assist growers in discriminating between clay soil types at a field and sub-field (e.g., hexagrid) level, advantageously preventing costly management mistakes. In general, the present techniques include collecting soil samples for a farm, to determine the clay composition at a granular level (e.g., using 8.5-meter hexagrids). The present techniques may compute mineralogical aspects/features, such as shrink swell potential, and a ratio of organic matter to cation exchange capacity.

The present techniques include methods and systems for collecting machine data and for determining clay types within one or more agricultural fields by analyzing the machine data. In some embodiments, the clay types may be encoded in spatial data files encoded in a suitable file format, such as a commercial or open source shapefile, a GeoJSON format, a Geography Markup Language (GML) file, etc. Such spatial data files may include one or more layers (i.e., map layers, wherein each layer represents an agricultural characteristic (e.g., elevation, clay type, etc.). The individual layer(s) and/or files may be shared between multiple computing devices of an agricultural company, provided or sold to customers, stored in a database, etc.

Exemplary Computing Environment

FIG. 1 depicts an exemplary computing environment 100 in which the techniques disclosed herein may be implemented, according to an embodiment.

The environment 100 includes a client computing device 102, an implement 104, a remote computing device 106, and a network 108. Some embodiments may include a plurality of client computing devices.

The client computing device 102 may be an individual server, a group (e.g., cluster) of multiple servers, or another suitable type of computing device or system (e.g., a collection of computing resources). For example, the client computing device 102 may be a mobile computing device (e.g., a server, a mobile computing device, a smart phone, a tablet, a laptop, a wearable device, etc.). In some embodiments the client computing device 102 may be a personal portable device of a user. In some embodiments the client computing device 102 may be temporarily or permanently affixed to the implement 104. For example, the client computing device 102 may be the property of a customer, an agricultural analytics (or "agrilytics") company, an implement manufacturer, etc.

The client computing device 102 includes a processor 110, a memory 112 and a network interface controller (NIC) 114. The processor 110 may include any suitable number of processors and/or processor types, such as CPUs, one or more graphics processing units (GPUs), etc. Generally, the processor 110 is configured to execute software instructions stored in a memory 112. The memory 112 may include one or more persistent memories (e.g., a hard drive/solid state memory) and stores one or more set of computer executable instructions/modules, including a data collection module 116, a mobile application module 118, and an implement control module 120, as described in more detail below. More or fewer modules may be included in some embodiments. The NIC 114 may include any suitable network interface controller(s), such as wired/wireless controllers (e.g., Ethernet controllers), and facilitate bidirectional/multiplexed networking over the network 108 between the client computing device 102 and other components of the environment 100 (e.g., another client computing device 102, the implement 104, the remote computing device 106, etc.).

The one or more modules stored in the memory 112 may include respective sets of computer-executable instructions implementing specific functionality. For example, in an embodiment, the data collection module 116 includes a set of computer-executable instructions for collecting a machine data set from an implement (e.g., the implement 104). The data collection module 116 may include instructions for collecting an above-ground and/or below-ground soil sample.

The machine data collection module 116 may include a respective set of instructions for retrieving/receiving data from a plurality of different implements. For example, a first set of instructions may be for retrieving/receiving machine data from a first tractor manufacturer, while a second set of instructions is for retrieving/receiving machine data from a second tractor manufacturer. In another embodiment, the first and second set of instructions may be for, respectively, receiving/retrieving data from a tiller and a harvester. Of course, some libraries of instructions may be provided by the manufacturers of various implements and/or attachments, and may be loaded into the memory 112 and used by the data collection module 116. The data collection module 116 may retrieve/receive machine data from a separate hardware device (e.g., a client computing device 102 that is part of the implement 104) or directly from one or more of the sensors of the implement 104 and/or one or more of the attachments 130 coupled to the implement 104, if any.

The machine data may include any information generated by the client computing device 102, the implement 104 and/or the attachments 130. In some cases, the machine data may be retrieved/received via the remote computing device 106 (e.g., from a third-party cloud storage platform). For example, the machine data may include a clay type generated by analyzing a soil sample using a soil analysis attachment 130. The machine data may include sensor measurements of engine load data, fuel burn data, draft, fuel consumption, wheel slippage, etc. The machine data may include one or more time series, such that one or more measured values are represented in a single data set at a common interval (e.g., one-second). For example, the machine data may include a first time series of draft at a one-second interval, a second time series of wheel slippage, etc.

The machine data may be location-aware. For example, the client computing device 102 may add location metadata to the machine data, such that the machine data reflects an absolute and/or relative geographic position (i.e., location, coordinate, offset, heading, etc.) of the client computing device 102, the implement 104, and/or the attachments 130 within the agricultural field at the precise moment that the client computing device 102 captures the machine data. It will also be appreciated by those of ordinary skill in the art that some sensors and/or agricultural equipment may generate machine data, that is received by the client computing device 102 that already includes location metadata added by the sensors and/or agricultural equipment. In an embodiment wherein the machine data comprises a time series, each value of the time series may include a respective geographic metadata entry. It will be further appreciate by those of ordinary skill in the art that when the machine data is received from a historical archive, the machine data may include historical location data (e.g., the GPS coordinates corresponding to the location from which the historical machine data was captured).

The data collection module 116 may receive and/or retrieve the machine data via an API through a direct hardware interface (e.g., via one or more wires) and/or via a network interface (e.g., via the network 108). The data collection module 116 may collect (e.g., pull the machine data from a data source and/or receive machine data pushed by a data source) at a predetermined time interval. The time interval may be of any suitable duration (e.g., once per second, once or twice per minute, every 10 minutes, etc.). The time interval may be short, in some embodiments (e.g., once every 10 milliseconds). The data collection module 116 may include instructions for modifying and/or storing the machine data. For example, the data collection module 116 may parse the raw machine data into a data structure. The data collection module 116 may write the raw machine data onto a disk (e.g., a hard drive in the memory 112).

In some embodiments, the data collection module 116 may transfer the raw machine data, or modified machine data, to a remote computing system/device, such as the remote computing device 106. The transfer may, in some embodiments, take the form of an SQL insert command. In effect, the data collection module 116 performs the function of receiving, processing, storing, and/or transmitting the machine data. The data collection module 116 may receive (e.g., from a soil probe attachment) soil sample data corresponding to one or more points within the machine data.

The mobile application module 118 may include computer-executable instructions that display one or more graphical user interfaces (GUIs) on the output device 124 and/or receive user input via the input device 122. For example, the mobile application module 118 may correspond to a mobile computing application (e.g., an Android, iPhone, or other) computing application of an agrilytics company. The mobile computing application may be a specialized application corresponding to the type of computing device embodied by the client computing device 102. For example, in embodiments where the client computing device 102 is a mobile phone, the mobile application module 118 may correspond to a mobile application downloaded for iPhone. When the client computing device 102 is a tablet, the mobile application module 118 may correspond to an application with tablet-specific features. Exemplary GUIs that may be displayed by the mobile application module 118, and with which the user may interact, are discussed below.

The mobile application module 118 may include instructions for receiving/retrieving mobile application data from the remote computing device 106. In particular, the mobile application module 118 may include instructions for transmitting user-provided login credentials, receiving an indication of successful/unsuccessful authentication, and other functions related to the user's operation of the mobile application. The mobile application module 118 may include instructions for receiving/retrieving, rendering, and displaying visual maps in a GUI. Specifically, the application module 118 may include computer-executable instructions for displaying one or more map layers in the output device 124 of the client computing device 102. The map layers may depict, for example, one or more clay types within an agricultural field.

The implement control module 120 includes computer-executable instructions for controlling the operation of an implement (e.g., the implement 104) and/or the attachments 130. The implement control module 120 may control the implement 104 while the implement 104 and/or attachments 130 are in motion (e.g., while the implement 104 and/or attachments 130 are being used in a farming capacity). For example, the implement control module 120 may include an instruction that, when executed by the processor 110 of the client computing device 102, causes the implement 104 to accelerate or decelerate, or collect a soil sample using a soil probe.

In some embodiments, the implement control module 120 may cause one of the attachments 130 to raise or lower the disc arm of a tiller, or to apply more or less downward or upward pressure on the ground. In some embodiments, the implement control module 120 may control the attachments 130 in response to clay type of the agricultural field where the implement 130 is positioned. Practically, the implement control module 120 has all of the control of the implement 104 and/or attachments 130 as does the human operator.

The implement control module 120 may include a respective set of instructions for controlling a plurality of implements. For example, a first set of instructions may be for controlling an implement of a first tractor manufacturer, while a second set of instructions is for controlling an implement of a second tractor manufacturer. In another embodiment, the first and second set of instructions may be for, respectively, controlling a tiller and a harvester. Of course, many configurations and uses are envisioned beyond those provided by way of example.

In some embodiments, the implement control module 120 may include computer-executable instructions for executing one or more agricultural prescriptions with respect to a field. For example, the control module 120 may execute an agricultural prescription that specifies, for a given agricultural field, a varying application rate of a chemical (e.g., a fertilizer, an herbicide, a pesticide, etc.) or a seed to apply at various points along the path based on the clay characteristics of the field. The control module 120 may analyze the current location of the implement 104 and/or the attachments 130 in real-time (i.e., as the control module 120 executes the agricultural prescription).

In some embodiments, one or more components of the computing device 102 may be embodied by one or more virtual instances (e.g., a cloud-based virtualization service). In such cases, one or more client computing device 102 may be included in a remote data center (e.g., a cloud computing environment, a public cloud, a private cloud, etc.). For example, a remote data storage module (not depicted) may remotely store data received/retrieved by the computing device 102. The client computing device 102 may be configured to communicate bidirectionally via the network 108 with the implement 104 and/or an attachments 130 that may be coupled to the implement 104. The implement 104 and/or the attachments 130 may be configured for bidirectional communication with the client computing device 102 via the network 108.

The client computing device 102 may receive/retrieve data (e.g., machine data) from the implement 104, and/or the client computing device 102 may transmit data (e.g., instructions) to the implement 104. The client computing device 102 may receive/retrieve data (e.g., machine data) from the attachments 130, and/or may transmit data (e.g., instructions) to the attachments 130. The implement 104 and the attachments 130 will now be described in further detail.

The implement 104 may be any suitable powered or unpowered equipment/machine or machinery, including without limitation: a tractor, a combine, a cultivator, a cultipacker, a plow, a harrow, a stripper, a tiller, a planter, a baler, a sprayer, an irrigator, a sorter, an harvester, etc. The implement 104 may include one or more sensors (not depicted) including one or more soil probe and the implement 104 may be coupled to one or more attachments 130. For example, the implement 104 may include one or more sensors for measuring respective implement values of engine load data, fuel burn data, draft sensing, fuel consumption, wheel slippage, etc. Many embodiments including more or fewer sensors measuring more or fewer implement values are envisioned. The implement 104 may be a gas/diesel, electric, or hybrid vehicle operated by a human operator and/or autonomously (e.g., as an autonomous/driverless agricultural vehicle).

The attachments 130 may be any suitable powered or unpowered equipment/machinery permanently or temporarily affixed/attached to the implement 104 by, for example, a hitch, yoke or other suitable mechanism. The attachments 130 may include any of the types of equipment that the implement 104 may comprise (e.g., a tiller). The attachments 130 may include one or more sensors (not depicted) that may differ in number and/or type according to the respective type of the attachments 130 and the particular embodiment/scenario. For example, a tiller attachment 120 may include one or more soil coring probes. It should be appreciated that many attachments 130 sensor configurations are envisioned. For example, the attachments 130 may include one or more cameras. The attachments 130 may be connected to the implement 104 via wires or wirelessly, for both control and communications. For example, attachments 130 may be coupled to the client computing device 102 of the implement 104 via a wired and/or wireless interface for data transmission (e.g., IEEE 802.11, WiFi, etc.) and main/auxiliary control (e.g., 7-pin, 4-pin, etc.). The client computing device 102 may communicate bidirectionally (i.e., transmit data to, and/or receive data from) with the remote computing device 106 via the network 108.

The client computing device 102 includes an input device 122 and an output device 124. The input device 122 may include any suitable device or devices for receiving input, such as one or more microphone, one or more camera, a hardware keyboard, a hardware mouse, a capacitive touch screen, etc. The output device 124 may include any suitable device for conveying output, such as a hardware speaker, a computer monitor, a touch screen, etc. In some cases, the input device 122 and the output device 124 may be integrated into a single device, such as a touch screen device that accepts user input and displays output. The client computing device 102 may be associated with (e.g., leased, owned, and/or operated by) an agrilytics company.

The network 108 may be a single communication network, or may include multiple communication networks of one or more types (e.g., one or more wired and/or wireless local area networks (LANs), and/or one or more wired and/or wireless wide area networks (WANs) such as the Internet). The network 108 may enable bidirectional communication between the client computing device 102 and the remote computing device 106, or between multiple client computing devices 102, for example.

The remote computing device 106 includes a processor 140, a memory 142, and a NIC 144. The processor 140 may include any suitable number of processors and/or processor types, such as CPUs and one or more graphics processing units (GPUs). Generally, the processor 140 is configured to execute software instructions stored in the memory 142. The memory 142 may include one or more persistent memories (e.g., a hard drive/solid state memory) and stores one or more set of computer executable instructions/modules, as discussed below. For example, the remote computing device 106 may include a data processing module 150, a topographic module 152, a mineral composition module 154, a clay characterization module 156, and a prescription module 158. The NIC 144 may include any suitable network interface controller(s), such as wired/wireless controllers (e.g., Ethernet controllers), and facilitate bidirectional/multiplexed networking over the network 106 between the remote computing device 106 and other components of the environment 100 (e.g., another remote computing device 106, the client computing device 102, etc.).

The one or more modules stored in the memory 142 may include respective sets of computer-executable instructions implementing specific functionality. For example, in an embodiment, the data processing module 150 includes computer-executable instructions for receiving/retrieving data from the client computing device 102, the implement 104, and/or the attachments 130. For example, the data processing module 150 may include instructions that when executed by the processor 140, cause the remote computing device 106 to receive/retrieve machine data. The data processing module 150 may include further instructions for storing the machine data in one or more tables of the database 180. The data processing module 150 may store raw machine data, or processed data.

The data processing module 150 may include instructions for processing the raw machine data to generate processed data. For example, the processed data may be data that is represented using data types data of a programming language (e.g., R, C#, Python, JavaScript, etc.). The data processing module 150 may include instructions for validating the data types present in the processed data. For example, the data processing module 150 may verify that a value is present (i.e., not null) and is within a particular range or of a given size/structure. In some embodiments, the data processing module 150 may transmit processed data from the database 180 in response to a query, or request, from the client computing device 102. The data processing module 150 may transmit the processed data via HTTP or via another data transfer suitable protocol.

The topographic module 152 may include instructions for retrieving and/or providing mapping data (e.g., electronic map layer objects) to other modules in the remote computing device 106. The mapping data may take the form of raw data (e.g., a data set representing clay composition map for a spatial area). In some embodiments, the topographic module may include spatial data files. The topographic module 152 may store mapping data in, and retrieve mapping data from, the database 180. The topographic module 152 may source elevation data from public sources, such as the United States Geological Survey (USGS) National Elevation Dataset (NED) database. In some embodiments, the data processing module 150 may provide raw data to the topographic module 152, wherein instructions within the topographic module 152 infer the elevation of a particular tract of land by analyzing the raw data. The elevation data may be stored in a two-dimensional (2D) or three-dimensional (3D) data format, depending on the embodiment and scenario.

The mineral composition module 154 may include instructions for analyzing one or more machine data variables to identify mineralogical features. As discussed, the machine data generated by the implement 104 and/or the attachments 130 may include measurements corresponding to a soil probe. The mineralogical features may be identified directly, by analyzing soil samples, or by analyzing other data (e.g., historical machine data). For example, the soil probe may be used to generate a cation exchange capability value, an organic matter measurement, etc. with respect to a plurality of locations, or points, within a field. In some embodiments the points may correspond to a respective hexagonal grid cell within a tiled cell (i.e., a hexagrid). The mineral composition module may associate a soil sample with a respective hexagrid. In some embodiments, associating the soil sample may include reading machine data corresponding to the soil sample from the electronic soil probe. The mineral composition module may associate location data with the machine data corresponding to the soil sample.

The clay characterization module 156 may include analyzing the mineralogical features and/or machine data to determine clay characteristics. For example, the clay characterization may characterize a soil sample as belonging to a clay group, such as kaolin, smectite, illite, chlorite, etc. In some embodiments, the clay characterization module 156 may further identify the specific clay within the clay group, such as montmorillonite, nacrite, etc. In some embodiments, the clay characterization module 156 may determine clay characteristics of a soil sample by referencing a digital map layer, such as one provided by the topographic module 152. In some embodiments, the mineral composition module 154 and/or the clay characterization module 156 may analyze machine data using one or more trained machine learning models to determine clay characteristics of the field. In yet other embodiments, the clay characterization module 156 may provide a quantitative index of soil clay activity. For example, a soil clay characterization may include identification and/or quantification of soil type within a given hexagrid of a land tract. A single hexagrid may include multiple soil clay characterizations, each including respective quantifications of the soil clay activity.

The prescription module 158 includes computer-executable instructions for generating one or more agricultural prescriptions. The agricultural prescriptions may be a set of computer-executable instructions for performing one or more agricultural interventions with respect to an agricultural field. For example, the agricultural prescription may include one more map layers specifying a respective set of interventions relating to seeding, fertilization, tillage, etc. The client computing device 102 may receive/retrieve the prescription instructions, and execute them.

The prescription module 158 may include generating one or more agricultural prescriptions, or scripts. The agricultural prescriptions may include computer-executable instructions for causing an implement (e.g., the implement 130) to perform one or more tasks (e.g., dispense a macronutrient fertilizer at a predetermined and/or variable rate). In some embodiments, the prescription may include instructions for performing the tasks in response to a clay type at a location within a given field. For example, the implement control module 120 may analyze a field map layer received from the topographic module 152 and a clay map layer received from the clay characterization module 156. The implement control module 120 may execute the prescription. The prescription may include instructions causing the implement 130 to perform the task in a predetermined way (e.g., apply fertilizer at 0.1 gallons/second) when 1) the location of the implement 130 coincides with a clay type in the clay map layer, as determined by reference to the clay map layer; and 2) the location of the implement 130 coincides with a particular field, as determined by reference to the field map layer. In this way, the prescription module 158 may generate prescriptions executable by a client device for modifying a clay soil to include, for example, more of a given macronutrient (e.g., potassium).

The prescription module 158 may be generated by a suitable tool. For example, in some embodiments, the remote computing device 106 may include a further module that allows the user to specify the number of years desired to build soil potassium to a critical/target level. The prescription module 158 may include instructions for calculating, based on the target rate and the current rate as seen in the machine data, an amount of macronutrient to apply to cause the soil to reach the target value.

The remote computing device 106 may further include one or more databases 180, an input device 182, and an output device 184. The database 180 may be implemented as a relational database management system (RDBMS) in some embodiments. For example, the data store 180 may include one or more structured query language (SQL) databases, a NoSQL database, a flat file storage system, or any other suitable data storage system/configuration. In general, the database 180 allows the client computing device 102 and/or the remote computing device 106 to create, retrieve, update, and/or retrieve records relating to performance of the techniques herein. For example, the database 180 may allow the client computing device 102 to store information received from one or more sensors of the implement 104 and/or the attachments 130. The database 180 may include a Lightweight Directory Access Protocol (LDAP) directory, in some embodiments. The client computing device 102 may include a module (not depicted) including a set of instructions for querying an RDBMS, an LDAP server, etc. For example, the client computing device 102 may include a set of database drivers for accessing the database 180 of the remote computing device 106. In some embodiments, the database 180 may be located remotely from the remote computing device 104, in which case the remote computing device 104 may access the database 180 via the NIC 112 and the network 106.

The input device 182 may include any suitable device or devices for receiving input, such as one or more microphones, one or more cameras, a hardware keyboard, a hardware mouse, a capacitive touch screen, etc. The input device 182 may allow a user (e.g., a system administrator) to enter commands and/or input into the remote computing device 106, and to view the result of any such commands/input in the output device 184. For example, an employee of the agrilytics company may use the input device 182 to adjust parameters with respect to one or more agricultural fields for applying macronutrients via a prescription.

The output device 184 may include any suitable device for conveying output, such as a hardware speaker, a computer monitor, a touch screen, etc. The remote computing device 106 may be associated with (e.g., leased, owned, and/or operated by) an agrilytics company. As noted above, the remote computing device 106 may be implemented using one or more virtualization and/or cloud computing services. One or more application programming interfaces (APIs) may be accessible by the remote computing device 106.

In operation, the agrilytics company may access the remote computing device 106 to establish one or more field records on behalf of one or more growers. For example, the company may store the field records in the database, wherein each grower is associated with a unique identifier (e.g., a universally unique identifier (UUID)) as are each of the grower's respective fields. For example, the grower may be associated with the grower's fields in the database via a one-to-many relationship.

The agrilytics company may populate the database 180 with machine data corresponding to the grower's fields by using the implement 104 to drive the fields and collect the machine data. The machine data may include information gathered from an attachment 130 (e.g., a soil probe) and/or machine data collected from other sources. Once the machine data for the grower's fields has been collected, the mineral composition module 154 may analyze the machine data to determine mineralogical features of the grower's one or more fields. The clay characterization module 156 may analyze the mineralogical features and determine one or more clay types corresponding to the field. The clay types may be assigned to one or more hexagrids within the field.

The prescription module 158 may include instructions that analyze the mineralogical composition and clay content of the field and determine one or more treatments for affecting portions of the field. For example, the prescription module 158 may be pre-programmed to increase the potassium content of each hexagrid to a specified critical level. When the organic matter percentage of a given hexagrid is below the threshold, the prescription module 158 may include instructions for adding organic fertilizer to the hexagrid. The instructions for adding organic fertilizer may vary based on the clay type of the hexagrid. For example, in a clay type having higher cation exchange potential, the prescription module 158 may cause less fertilizer to be applied to increase the potassium level, as compared to another hexagrid having a lower cation exchange potential. It should be appreciated that the examples provided are intentionally simplified for explanation, and many further embodiments are envisioned, as described below.

Exemplary Clay Sampling Embodiments

Figure 2:
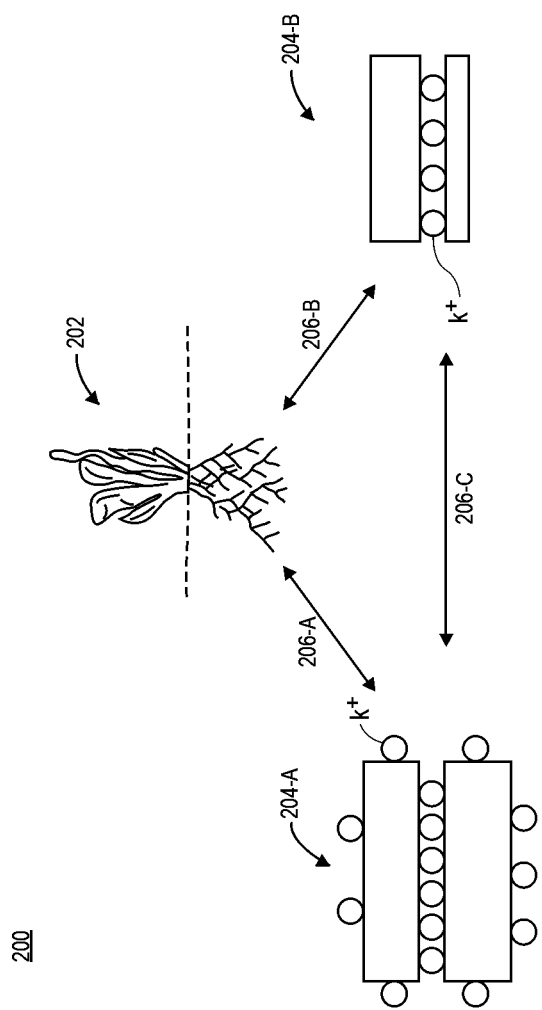
FIG. 2 depicts an exemplary crop growing environment depicting clay types, according to an embodiment.

FIG. 2 depicts an exemplary crop growing environment 200 depicting clay types, according to an embodiment. The crop growing environment 200 includes a crop 202, a plurality of clay lattices 204 and a plurality of cation exchange pathways 206. The crop 202 may be, for example, a cereal crop (e.g., corn, wheat, rice, etc.) a tuber crop (e.g., sweet potato), a vegetable crop (e.g., onion, tomato, etc.), a fruit crop (e.g., mangoes, grapes, etc.). The crop 202 may include an above-ground portion and/or a below-ground portion.

The plurality of clay lattices 204 may include a clay lattice 204-A that includes free/exchangeable cations (e.g., potassium cations (K+)). The exchangeable cations may be located between/within layers, or sheets, of the clay lattice 204-A and/or about the sheets composing the clay lattice 204-A. The clay lattice 204-A may be a smectitic clay such as montmorillonite, kaolinite, etc. The clay lattice 204-A may exchange the exchangeable cations with the crop 202 via the cation exchange pathway 206-A, and/or with other clay lattices via the cation exchange pathway 206-C.

The plurality of clay lattices 204 may include a clay lattice 204-B that includes fixed, or captured, cations. For example, the captured cations may include potassium (K+) cations. The clay lattice 204-B may be a silicate clay (e.g., a mica clay, a vermiculite clay, a 2:1 clay, etc.) that traps the exchangeable cations, preventing the cations from being exchanged along the cation exchange pathway 206-B or the cation exchange pathway 206-C. The cations may be trapped within the clay lattices as discussed below. In some cases, the clay lattice 204-B may allow the cations to be released, albeit more slowly. The lack of exchange may be referred to as cation fixation.

The plurality of exchange pathways 206 within the crop growing environment 200 allow the cations to be exchanged between the clay lattices 204-A and the crop 202. For example, the crop 202 may uptake potassium ions from the clay lattice 204-A. The rate of uptake may determine the level of a given macronutrient available to the crop 202. In other cases, soluble cations may be leached away from the crop 202 and/or the plurality of clay lattices 204. In still further cases soluble cations may be unavailable due to depleted plant available water. The present techniques may include measuring and treating the environment 200, for example, to add macronutrients in the form of fertilizer (e.g., a potassium fertilizer).

Figure 3:
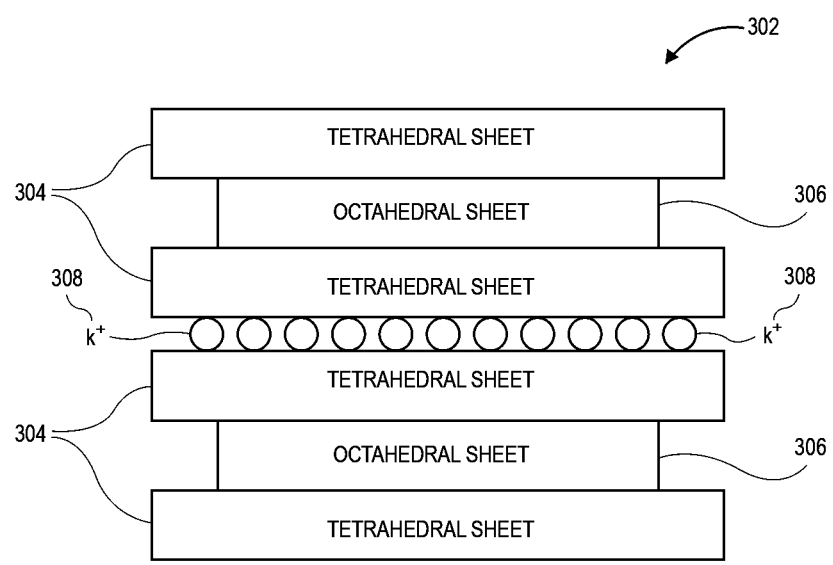
FIG. 3 depicts an exemplary 2:1 clay, according to one embodiment and scenario.

FIG. 3 depicts an exemplary 2:1 clay 302, according to one embodiment and scenario. The 2:1 clay 302 includes a plurality of tetrahedral sheets 304 and a plurality of octahedral sheets 306, in a ratio of two tetrahedral sheets per one octahedral sheet. When the 2:1 clay 302 is a potassium fixating clay, as discussed with respect to FIG. 2, the 2:1 clay 302 may include a plurality of cations 308 (e.g., potassium ions). The plurality of cations may be captured, or fixed, between two or more of the plurality of tetrahedral sheets 304. The plurality of tetrahedral sheets 304 and the plurality of octahedral sheets 306 in a ratio of 2:1 may cause cation macronutrients needed for growth of a crop (e.g., the crop 202) to be trapped in holes, or openings, in the lattice structure of the 2:1 clay 302. In some clays, nutrients can move in and out. However, when the clays become dehydrated, holes within the clays collapse, trapping some ions (e.g., potassium) but allowing others to be freed (e.g., calcium, magnesium, etc.). The ability of the clay to hold particular ions depends on the size of gaps in the crystalline structure of the clays.

As noted, the present techniques may include analyzing properties of the plurality of cations 308 using a soil probe implement. For example, in an embodiment, the implement 104 may include a probe attachment 130 that samples the soil of the field at different points. The sampling may include generating a dataset corresponding to the field, divided into hexagonal regions (e.g., a set of one or more hexagrids). The sampling may include analyzing one or more samples within each hexagrid to determine the absorptive properties (e.g., exchange free energy) of each sample. By computing such properties, the present techniques may be used to determine an appropriate treatment regime and/or to compare each sample to other measured soils. For example, a montmorillonite soil in Missouri may be compared to a montmorillonite soil in Indiana. In some embodiments, the present techniques may include analyzing additional factors of the field (e.g., historical field intervention, weather data, etc.).

Exemplary Clay Mapping Embodiments

Figure 4:
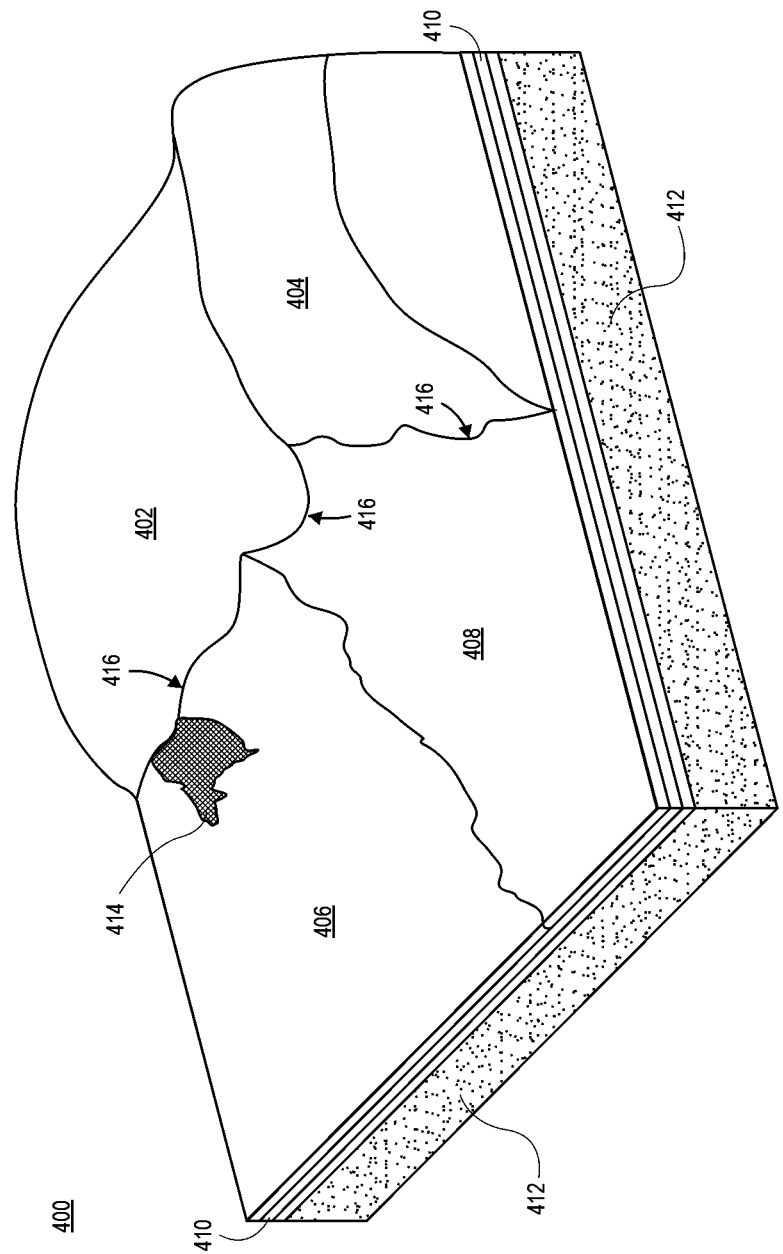
FIG. 4 depicts an exemplary field map layer corresponding to an agricultural field, according to an embodiment.

FIG. 4 depicts an exemplary field map layer 400 corresponding to an agricultural field. The field map layer 400 may correspond to a digital map layer downloaded from, for example, the remote computing device 106 of FIG. 1. The field map layer 400 may be a digital map layer displayed in a device (e.g., the client computing device 102 of FIG. 1). The field map layer 400 may correspond to a field being driven by the implement 104, for example. The implement 104 may drive the field corresponding to the field map layer 400, collecting one or more soil samples from the agricultural field. The field map layer 400 may include a field region 402, a field region 404, a field region 406 and a field region 408. The field map layer 400 may include any suitable number of regions in some embodiments. The regions may be encoded using hexagrids. For example, the hexagrid 402 may be subdivided into a plurality of one or more hexagrids (e.g., 8.5-m hexagonal cells).

The field map layer 400 may include one or more subsurface field regions 410 and one or more bedrock field regions 412. The subsurface field regions 410 and bedrock field regions 412 may be depicted as separate map layers in some embodiments. The field map layer 400 may include a waterway field region 414. The waterway field region 414 may correspond to a portion of a flowing surface waterway, such as a stream, river, delta, swamp, etc. In some embodiments, the waterway field region 414 may correspond to a historical waterway, such as an alluvium or estuary created during a glacial period.

The field map layer 400 may be generated by sampling the agricultural field. For example, the grower may drive the field corresponding to the field map layer 400 and collect a plurality of samples of the agricultural field, including respective machine data. For example, the field may be sampled according to the hexagrid subdivisions, such that one or more soil probe samples are collected from each hexagonal subdivision of the agricultural field. The present techniques may include analyzing the samples to determine one or more clay types among the regions of the field, as shown in FIG. 5.

Figure 5:
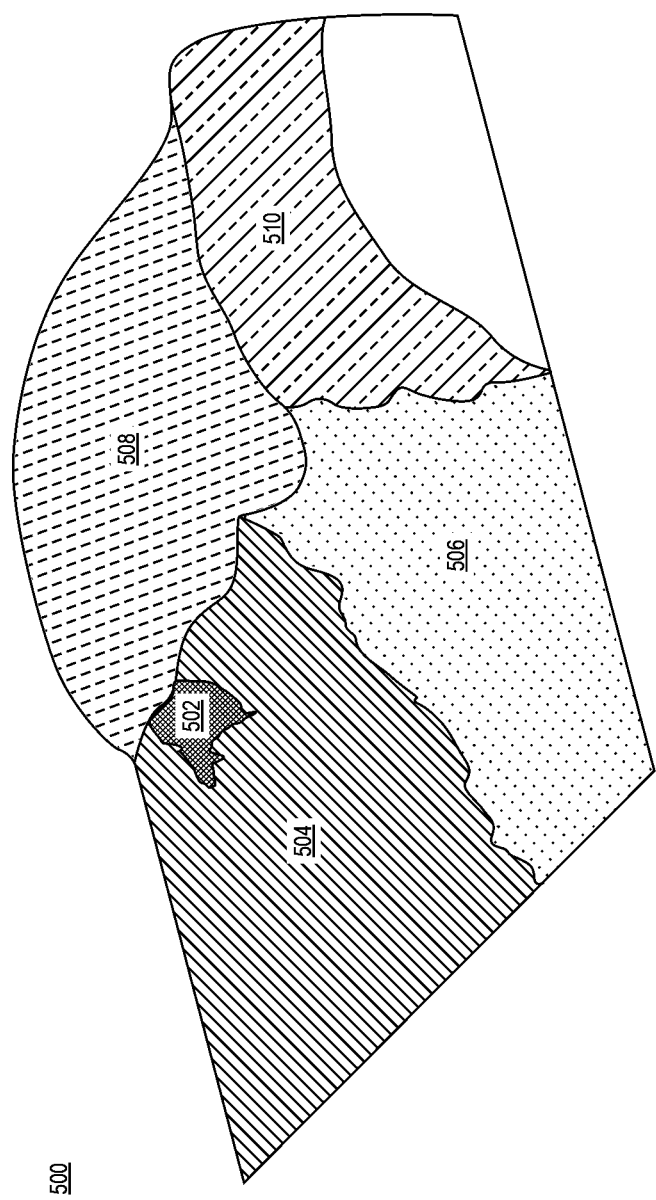
FIG. 5 depicts a field map layer depicting multiple determined clay types corresponding to the agricultural field shown in FIG. 4, according to one embodiment and scenario.

FIG. 5 depicts a field map layer 500 depicting multiple determined clay types corresponding to the agricultural field shown in FIG. 4. For example, a field region 502 may correspond to the waterway field region 414 of FIG. 4. The present techniques may include identifying one or more clay soil types present within the field region 502 that may depend on the geologic features of the field region 502. For example, when the waterway field region 414 corresponds to an historical alluvial area, heavy 2:1 clay soil may be found. The heavy 2:1 clay soil may include a very fine soil with minute particle sizes that are finely precipitated. Another region, such as the field region 504 may be found to have soil with a greater amount of silt, resulting in a silty clay loam. Yet another field region such as the field region 506 may be a weathered region that is closer to a 1:1 clay.

A given field (e.g., the field corresponding to the field map layer 500) may include a mixture of clays of significantly varying ratios, even within a relatively small growing area (e.g., a 10-acre farm). Such variability may be the result of distant (e.g., glacial) activity and/or more recent activity (e.g., weathering) caused by areas at lower-lying elevation receiving more standing water.

By identifying the differences in clay types, the present techniques may prevent growers from making a large mistake due to varying cation-exchange capability and/or water holding properties of the various clays, including the absorption and shrink-swell capacity of the clays in respective field regions. Regardless of the cause of such variation, it is essential that growers are able to quickly appreciate the differences in soil properties, such as organic matter to cation exchange capability ratio. For example, soil in Illinois regularly measures 3.5% organic matter with cation exchange capability of +20. In the Mississippi delta, organic matter may measure 2% (or less) with cation exchange capability of >=30. The present techniques improve grower yields and agricultural product performance by allowing the grower to generate large data sets for representing clay type information through automated collection and processing of machine data, and for generating visualizations based on that collection/processing to allow the grower to understand how clay types will cause cations to be exchanged/bound up in soil, and to automatically generate prescriptions to modify the soil composition.

The field map layer 500 including identified clay types may be displayed in a graphical user interface (GUI). For example, the GUI may be displayed in the mobile application 118. The GUI may also depict one or more pieces of growing equipment, such as the implement 104. Thus, when the grower is driving the field, the GUI may depict the location of the grower and/or the implement with respect to the one or more field regions (e.g., the field region 504). The present techniques may include using the GUI for autonomous and/or operator-controlled application of one or more field interventions, such as during the execution of agricultural prescriptions. The present techniques advantageously allow the grower to visualize differing clay types within areas of the agricultural field.

Exemplary Computer-Implemented Methods

Figure 6:
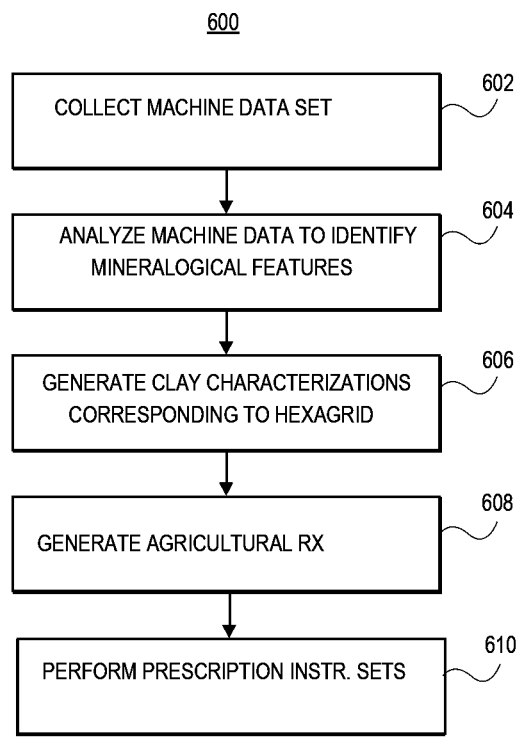
FIG. 6 depicts a flow diagram of a computer-implemented method of improving agricultural treatment application in clay soils within an agricultural field, according to one embodiment and scenario.

FIG. 6 depicts a flow diagram of an example computer-implemented method 600 for improving agricultural treatment application in clay soils within an agricultural field, according to one embodiment and scenario.

The method 600 may include collecting a machine data set corresponding to the agricultural field (block 602). The machine data set corresponding to the agricultural field may include one or more measurements taken using a soil probe. The soil probe may include manual, hydraulic and/or electronic aspects, in some embodiments and scenarios. Specifically, the implement 104 may collect machine data using the soil probe. In some embodiments, the collected machine data set may include historical machine data collected previously. The historical machine data may be collected by the implement 104 or another process/actor, in some embodiments. The machine data may include data collected from multiple mechanisms (e.g., from farm equipment, from one or more soil probes, and/or other sources).

The method 600 may include analyzing the machine data set to identify one or more mineralogical features (block 604). The mineralogical features may include shrink swell potential, organic matter content, cation exchange capacity, soil texture, and/or other physical properties and/or chemical properties of the soil, nitrogen mineralization, pore space size, water content, alkalinity, salinity, etc. In some embodiments, analyzing the machine data may include processing the machine data using a set of instructions for classifying the mineralogical features into one or more categories using a trained machine learning model (e.g., a classification machine learning model). The method 600 may include training the machine learning model using a labeled data set (e.g., in a machine learning module of the remote computing device 106). The method 600 may include operating the machine learning model using the machine data as input. Those of ordinary skill in the art will appreciate that other means for analyzing the machine data set, including computer vision-based approaches and/or other optical techniques may be used in some embodiments for generating some mineralogical features.

The method 600 may include generating a set of clay characterizations by analyzing the mineralogical features, each of the characterizations corresponding to a respective hexagrid cell (block 606). As noted above, the collection of machine data may be performed by an implement (e.g., the implement 104) and/or by retrieving/receiving digital machine data. In either case, the method 600 may annotate each data point within the machine data with a geographic position. The geographic position of each point may be added to the machine data upon collection by an implement and/or a computing device (e.g., by an onboard Global Positioning System (GPS) device of the implement 130 or the client computing device 106). Once annotated with location information, the machine data can be fixed within a field grid. In some embodiments, it may be advantageous to subdivide the field (e.g., the field corresponding to the field map layer 600 of FIG. 6) into hexagonal grids (e.g., 8.5-meter hexagrids).

The method 600 may associate each hexagrid with the generated clay characterizations, such that once the method 600 has been completed, each of the hexagrids within the field include a respective set of clay characterizations. In this way, the grower, field manager, trusted advisor or other relevant party can view the field map layer showing respective clay characteristics for the field, as shown in FIG. 6. The ability to view differing clay characteristics is advantageous for practical growing purposes. In the most basic example, the grower operating the implement 104 may view the field map layer including clay characterizations and manually dispense more fertilizer in areas that are of a clay type likely to include more cation fixation. In other words, dispense more product in an area of the field likely to have lesser availability of a particular macronutrient. In further embodiments, the field map layer may be annotated with indications in color or using another suitable style depicting clay with likely good levels of macronutrient (e.g., a green color), reduced but still acceptable levels of macronutrient (e.g., a yellow color) and lacking levels of macronutrient (e.g., a red color). Therefore, even if the grower does not appreciate the relationship between clay characteristics and macronutrient profile, the visual indicators provide information sufficient for good decision making and improved economy of fertilizers and other treatments, in addition to improved yield per acre.

As discussed above, the method 600 may include generating and transmitting (e.g., from the remote computing device 106) the map layers via the network 108 for display in the client computing device 106. In still further embodiments, the present techniques may be used, optionally in conjunction with other non-clay characteristics map layers, to automate the application of agricultural treatments.

For example, the method 600 may include generating an agricultural prescription for the agricultural field, including at least one treatment based on the clay characterization (block 608). As discussed, the skilled grower will appreciate that certain clay types may include a clay lattice (e.g., the clay lattice 204-B) that includes fixed, or captured, cations. These clays may be 2:1 clays or other clay types that may inhibit the movement of nutrients necessary for plant growth. And as noted, the grower could manually activate a treatment by, for example, causing a sprayer to apply fertilizer based on the grower's monitoring of a GUI while driving the field.

However, the present techniques represent a further advantageous improvement over conventional techniques that require the grower to maintain constant attention during the laborious planting and harvest seasons, that may be further challenging due to hot/cold weather, precipitation and, in many cases, working in darkness. To that end, the method 600 may include performing the generated agricultural prescription by, for example, transmitting the prescription in the form of an electronic prescription file to the client computing device 102 for execution in the implement control module 120. The agricultural prescription may include sets of instructions for automatically applying a treatment in portions of the field that correspond with certain clay characteristics.

The agricultural prescription may access a location module (e.g., a GPS module) of the client computing device 102 to determine the real-time position of the implement within the field, with respect to the field map layer associated with clay characteristics information. The agricultural prescription may include instructions for causing a pre-determined agricultural treatment to be applied to the field, for example by accessing an attachment (e.g., the attachment 130 of FIG. 1). In this way, the present techniques may be advantageously used to identify the clay soil characteristics of a field, which may be highly variable for the reasons discussed above. The present techniques may further advantageously be used to automatically apply treatment product based on the clay soil characteristics, to conserve product while increasing yields.

Additional Considerations

The following considerations also apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

It should also be understood that, unless a term is expressly defined in this patent using the sentence "As used herein, the term" "is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" is employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of ordinary skill in the art will appreciate still additional alternative structural and functional designs for implementing the concepts disclosed herein, through the principles disclosed herein. Thus, while particular embodiments and applications have been illustrated and described, it is to be understood that the disclosed embodiments are not limited to the precise construction and components disclosed herein. Various modifications, changes and variations, which will be apparent to those of ordinary skill in the art, may be made in the arrangement, operation and details of the method and apparatus disclosed herein without departing from the spirit and scope defined in the appended claims.

What is claimed:

1. A computer-implemented method of improving agricultural treatment application in clay soils within an agricultural field, comprising:
   collecting a machine data set corresponding to the agricultural field,
   analyzing the machine data set to identify one or more mineralogical features,
   generating a set of soil clay characterizations by analyzing the one or more mineralogical features, each of the soil clay characterizations corresponding to a respective hexagrid cell, and
   generating an agricultural prescription for the agricultural field, including at least one treatment based on one or more of the soil clay characterizations.

2. The computer-implemented method of claim 1, wherein the machine data set corresponding to the agricultural field includes one or more measurements taken using a soil probe.

3. The computer-implemented method of claim 1, wherein the one or more mineralogical features include a ratio of soil organic matter to cation exchange capacity.

4. The computer-implemented method of claim 1, further comprising:
   displaying, in a client computing device, a field map layer in a graphical user interface, the field map layer depicting a topology of the agricultural field.

5. The computer-implemented method of claim 1, further comprising:
   displaying, in a client computing device, a clay map layer in a graphical user interface, the clay map layer depicting one or more soil clay characteristics within the agricultural field.

6. The computer-implemented method of claim 1 wherein generating the agricultural prescription for the agricultural field includes adding a nutrient to affect the potential availability of the nutrient in the agricultural field.

7. The computer-implemented method of claim 1, further comprising:
   analyzing the geographic position of a growing implement and, when the growing implement is within the agricultural field, causing a pre-determined agricultural treatment to be applied to the field.

8. A computing system comprising:
   one or more processors; and
   one or more memories storing instructions that, when executed by the one or more processors, cause the computing system to:
   collect a machine data set corresponding to an agricultural field,
   analyze the machine data set to identify one or more mineralogical features,
   generate a set of soil clay characterizations by analyzing the one or more mineralogical features, each of the soil clay characterizations corresponding to a respective hexagrid cell, and
   generate an agricultural prescription for the agricultural field, including at least one treatment based on one or more of the soil clay characterizations.

9. The computing system of claim 8, wherein the machine data set corresponding to the agricultural field includes one or more measurements taken using a soil probe.

10. The computing system of claim 8, wherein the one or more mineralogical features include a ratio of soil organic matter to cation exchange capacity.

11. The computing system of claim 8, the one or more memories storing further instructions that when executed, cause the computing system to:
    display, in a client computing device, a field map layer in a graphical user interface, the field map layer depicting a topology of the agricultural field.

12. The computing system of claim 8, the one or more memories storing further instructions that when executed, cause the computing system to:
    display, in a client computing device, a clay map layer in a graphical user interface, the clay map layer depicting one or more soil clay characteristics within the agricultural field.

13. The computing system of claim 8, wherein generating the agricultural prescription for the agricultural field includes adding a nutrient to affect the potential availability of the nutrient in the agricultural field.

14. The computing system of claim 8, the one or more memories storing further instructions that when executed, cause the computing system to:
    analyze the geographic position of a growing implement and,
    cause, when the growing implement is within the agricultural field, a pre-determined agricultural treatment to be applied to the field by executing the agricultural prescription.

15. A non-transitory computer readable medium containing program instructions that when executed, cause a computer to:
    collect a machine data set corresponding to an agricultural field,
    analyze the machine data set to identify one or more mineralogical features,
    generate a set of soil clay characterizations by analyzing the one or more mineralogical features, each of the soil clay characterizations corresponding to a respective hexagrid cell, and
    generate an agricultural prescription for the agricultural field, including at least one treatment based on one or more of the soil clay characterizations.

16. The non-transitory computer readable medium of claim 15, wherein the machine data set corresponding to the agricultural field includes one or more measurements taken using a soil probe.

17. The non-transitory computer readable medium of claim 15, wherein the one or more mineralogical features include a ratio of soil organic matter to cation exchange capacity.

18. The non-transitory computer readable medium of claim 15, containing further program instructions that when executed, cause a computer to:

display, in a client computing device, a clay map layer in a graphical user interface, the clay map layer depicting one or more soil clay characteristics within the agricultural field.

19. The non-transitory computer readable medium of claim 15, wherein generating the agricultural prescription for the agricultural field includes adding a nutrient to affect the potential availability of the nutrient in the agricultural field.

20. The non-transitory computer readable medium of claim 15, containing further program instructions that when executed, cause a computer to:
   analyze the geographic position of a growing implement and,
   cause, when the growing implement is within the agricultural field, a pre-determined agricultural treatment to be applied to the field by executing the agricultural prescription.

* * * * *